United States Patent [19]

Adam et al.

[11] 4,235,771

[45] Nov. 25, 1980

[54] WATER SOLUBLE AGENTS EFFECTIVE AS IMMUNOLOGICAL ADJUVANTS FOR STIMULATING IN THE HOST THE IMMUNE RESPONSE TO VARIOUS ANTIGENS AND COMPOSITIONS, NOTABLY VACCINES CONTAINING SAID WATER SOLUBLE AGENTS

[75] Inventors: Arlette Adam, Palaiseau; Françoise Audibert, Neuilly; Louis Chedid; Jean Choay, both of Paris; Rita Ciorbaru, Montrouge; Fabrielle Ellouz, Bagneux; Dominique Juy, Paris; Pierre Lefrancier, Bures sur Yvette; Claude Merser, Olivet; Jean-François Petit, Paris; Pierre Sinay, Orleans; Edgar Lederer, Sceaux, all of France

[73] Assignee: Agence Nationale de Valorisation de la Recherche (ANVAR), France

[21] Appl. No.: 906,002

[22] Filed: May 15, 1978

Related U.S. Application Data

[62] Division of Ser. No. 516,991, Oct. 22, 1974, Pat. No. 4,186,194.

[30] Foreign Application Priority Data

Oct. 23, 1973 [FR] France ................................ 73 37806
Jul. 1, 1974 [FR] France ................................ 74 22909

[51] Int. Cl.³ .......................................... C07C 103/52
[52] U.S. Cl. ............................................. 260/112.5 R
[58] Field of Search ................................... 260/112.5 R

[56] References Cited

U.S. PATENT DOCUMENTS

| 4,082,736 | 4/1978 | Jones et al. ................... 260/112.5 R |
| 4,094,971 | 6/1978 | Chedid et al. ................. 260/112.5 R |

FOREIGN PATENT DOCUMENTS

| 2434231 | 2/1976 | Fed. Rep. of Germany .... 260/112.5 R |
| 2655500 | 6/1977 | Fed. Rep. of Germany .... 260/112.5 R |

OTHER PUBLICATIONS

Kotani, et al., Biken Journal, vol. 18, 105–111, (1973).
F. Audibert, et al., Cell. Immun., 21, 243–249, (1976).
J. Med. Chem., 9, 1966, 971–973.

*Primary Examiner*—Delbert R. Phillips
*Attorney, Agent, or Firm*—Weiser, Stapler & Spivak

[57] ABSTRACT

Water soluble agents effective as immunological adjuvants for stimulating in the host the immune response to various antigens, comprising an acyl-muramic acid group, wherein acyl means acetyl or glycolyl, and a short peptide chain linked to said acyl-muramic acid group, the first and second amino acids of said peptide chain being preferentially alanine and glutamic acid respectively.

28 Claims, No Drawings

WATER SOLUBLE AGENTS EFFECTIVE AS IMMUNOLOGICAL ADJUVANTS FOR STIMULATING IN THE HOST THE IMMUNE RESPONSE TO VARIOUS ANTIGENS AND COMPOSITIONS, NOTABLY VACCINES CONTAINING SAID WATER SOLUBLE AGENTS

This is a division of application Ser. No. 516,991, filed Oct. 22, 1974, now U.S. Pat. No. 4,186,194.

The invention relates to water soluble agents effective as immunological adjuvants for stimulating, in a host, the immune response to various kinds of antigens. The invention relates more particularly to adjuvant agents capable of enhancing and promoting the activity of weak immunogens.

More particularly the invention relates to agents effective as adjuvants, useful for the immunisation of men and warm blooded animals against bacterial, viral and parasitic infections, and against various tissue antigens, of normal or pathological origin, and for example against tumors.

Materials having adjuvant properties have been known for some time. For instance it is well known that materials such as mycobacterial cells and mycobacterial cell walls enhance the production of antibodies in the host and more particularly, increase the host resistance to infections caused by numerous micro-organisms. The known materials of this kind, such as Freund's complete adjuvant which contains whole mycobacterial cells, have been found undesirable for therapeutic usage, by reason of the highly objectionable reactions caused thereby. Thus they may enhance the host's sensitivity to endotoxins, cause a hypersensitivity to tuberculin, and induce granuloma, lymphoid hyperplasia and, under certain circumstances, an experimental polyarthritis in the rat. Moreover, prior to the present invention, adjuvants based on mycobacterial substances, were difficult to purify by reason of their insolubility.

There has already been described, for example in French Pat. No. 71 41610 filed Nov. 19, 1971, a process enabling the production of an adjuvant agent which is soluble and substantially free of the drawbacks which have been mentioned. In particular, and by way of example, such an adjuvant agent may be obtained by a process consisting essentially of cultivating a strain of mycobacteria, of Nocardia cells or of related mycroorganisms, of collecting the cells from the cultivated strain, of distrupting them, of recovering the broken cell walls, for example by differential centrifugation, of separating and removing the waxes, free lipids, proteins and nucleic acids, of digesting the delipidated material derived from the cell walls with a murolytic enzyme, such as lysozyme, of removing the solid residue and of collecting the aqueous fraction containing the abovesaid soluble agents. Purification follows and, at least in certain cases, according to the nature of the initial strain treated, an additional fraction of the agents is obtained, for example by subjecting the abovesaid aqueous fraction to filtration on a molecular sieve, for example on a column of polydextran gel or of a similar material, such as the gel sold under the trademark "Sephadex G75" or "Sephadex G50".

For instance, when the initial cultivated strain is a strain of *Mycobacterium smegmatis*, filtration of the aqueous fraction on "Sephadex G50" gives two successive elution peaks both containing substances possessing adjuvant properties.

It was indicated in the abovesaid patent application that the adjuvant concerned, more particularly that extracted from the first of the two above-mentioned elution peaks, was probably constituted by an oligomer whose monomeric unit corresponds substantially to that of the cell walls of the micro-organisms from which they were extracted, with the exception of their lipid portions which are very small, or even non-existant. It was also noted that the adjuvant agent contained in the second of the two above-mentioned elution peaks appeared to be constituted by an oligomer poor in neutral sugars or even free of the latter, and whose monomeric unit contains amino-sugars and amino-acids of the constituent polymers of the cell walls of the above-said micro-organisms, and, if necessary, small lipid portions.

These various adjuvant agents certainly showed considerable progress relative to the insoluble adjuvants which had been previously described. They are however constituted by mixtures and it may be thought that, apparently, these agents can only be obtained, for example by the application of the process which has been described above, from mycobacteria, Nocardiae, and micro-organisms which are related to them.

The invention relates to soluble adjuvant agents of low molecular weight, well defined chemically and which—at least as regards a part of these agents—may be obtained by synthesis. It has been noted besides that a part at least of these well-defined and low molecular weight adjuvant agents may be obtained—by the biochemical route—not only from micro-organisms which have been mentioned above, but also from other procaryotic bacteria, for example entero-bacteria, of which one conventional representative is *E-Coli*, or *Micrococcus roseus*.

The adjuvant agents according to the invention are constituted by a monomer or by an oligomer formed from this monomer, the latter being characterised in that it contains an N-acyl-muramic acid (N-acyl-Mur), in which the acyl group is of the glycolyl or acetyl type, and a peptide chain comprising from 2 to 8 amino-acids, the first of these aminoacids, which is linked to the N-acyl-muramic acid, being constituted by alanine, serine or glycine, and the second of these aminoacids by glutamic acid or aspartic acid.

The invention relates more particularly to the application of these agents to the manufacture of vaccines, of which they enhance the immunogen effect by their capacity to facilitate and multiply the production of antibodies with regard to the vaccinating antigens in the host organism, and consequently to vaccine compositions containing, in addition to an immunogen agent or a vaccinating antigen, such an adjuvant agent.

A first group of prefered adjuvant agents is constituted by those which contain N-acetylglucosamine (N-AcGlc), more particularly by those whose monomer is essentially constituted by at least one polysaccharidepolypeptide comprising an N-acyl-muramic acid unit (N-acyl-Mur) in which the acyl group is constituted by an acetyl or glycolyl group, and to which are attached, on the one hand, an N-acetylglucosamine unit (N-AcGlc) and, on the other hand, a peptide chain of which the first aminoacid, which is fixed to the N-acyl-muramic acid, is constituted by alanine, serine or glycine, and the second aminoacid is constituted by glutamic acid or aspartic acid, one of the carboxyl functions of this second amino-acid being either free, or amido, and the other acid function being included in a linkage with another amino-acid constituted by meso-α-

ε-diaminopimelic acid, lysine, γ-aminobutyric acid or by 3-hydroxy-diaminopimelic acid.

These adjuvant agents are essentially constituted by soluble fragments of peptidoglycans entering into the constitution of procaryotes cell walls.

Among these agents, there may be mentioned more particularly the polysaccharide-polypeptides of low molecular weight comprising in their formulae units of:

N-acetylglucosamine (N-AcGlc),

N-acyl-muramic acid (N-acyl-Mur), in which the acyl group is preferably of the glycolyl or acetyl type, L-alanine (L-Ala), D-alanine (D-Ala), D-glutamic acid (D-Glu), whose carboxyl group at the α position is either free, or substituted, in which case it preferably forms an amido group, meso-α-ε-diaminopimelic acid (Meso-DAP), of which one of the carboxylic groups is either free, or included in a peptide linkage, and of which the other carboxyl group is either free, or substituted, in which case it forms preferably an amide group.

Among the agents according to the invention, there may be mentioned more particularly those in which N-acetylglucosamine, N-acyl-muramic acid, L-alanine, D-glutamic acid, meso-α-ε-diaminopimelic acid and D-alanine occur in the following respective molar ratios (it being understood that the absence of the 6th figure in the ratios indicated below only signifies that the corresponding agent does not contain D-alanine.

1:1:1:1:1 (disaccharide-tripeptide)

1:1:1:1:1:1 (disaccharide-tetrapeptide)

1:1:2:2:2:1 (disaccharide-heptapeptide)

1:1:2:2:2:2 (disaccharide-octapeptide)

2:2:2:2:2:1 (tetrasaccharide-heptapeptide)

2:2:2:2:2:2 (tetrasaccharide-octapeptide).

Among the adjuvant agents according to the invention, are to be mentioned the disaccharides and tetrasaccharides whose formulae follow, it being understood that the abbreviations D-Glu and meso-DAP may envisage both D-glutamic and meso-α-ε-diamino-pimelic acid units which contain free carboxylic groups as well as those in which the same groups are amidated (to the extent where these groups are not included in peptide linkages), that is to say, as regards disaccharides

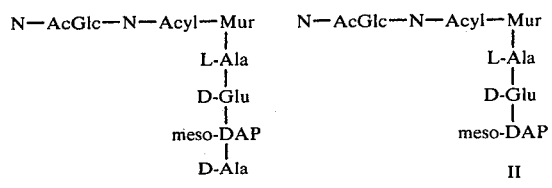

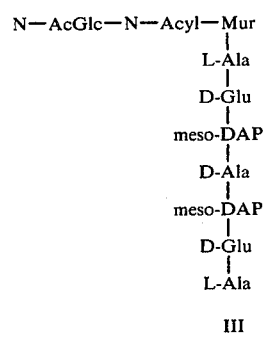

it being understood that the disaccharides of formula III contains, if necessary, in addition an additional D-alanine group fixed to the second of the meso-DAP units of the heptapeptide chain and, as regards tetrasaccharides

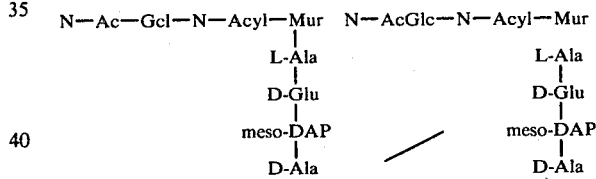

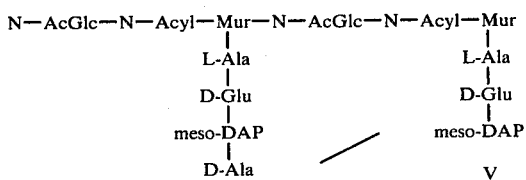

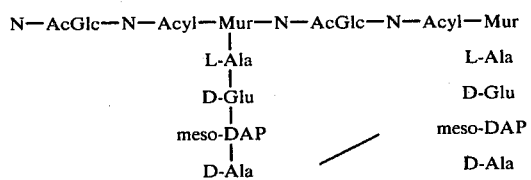

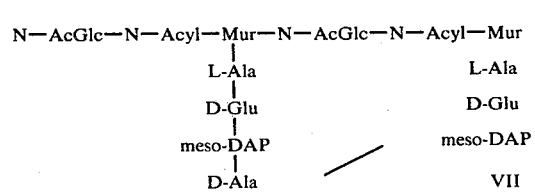

-continued

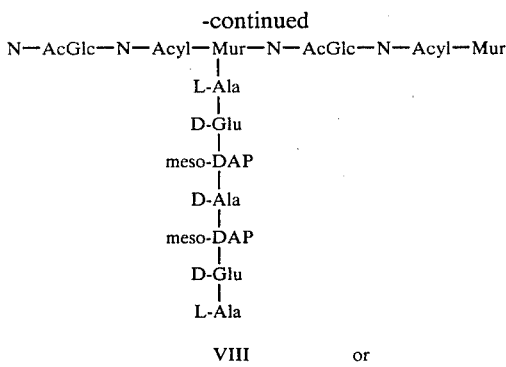

VIII or

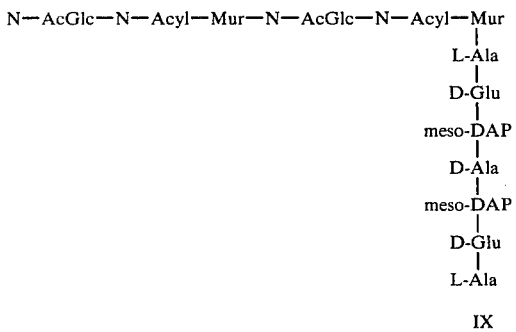

IX it being understood that the tetrasaccharides of formula VIII and IX comprise in addition, if necessary, a D-Ala group fixed to one of the meso-DAP groups of their heptapeptide chains.

The invention relates also to the oligomers formed, of which the monomeric units are directly derived from the formulae I to IX, for example those which contain from 3 to 6 monomeric units.

There is obtained in particular, from mycobacteria, for example from *Mycobacterium smegmatis,* the disaccharides or tetrasaccharides having the above-indicated formulae, in which the acyl units are glycolyl units, the carboxyl groups of the D-glutamic acid units are amidated and the α-ε-diaminopimelic acid units comprise a carboxylic group either free, or included in a peptide linkage, the other being amidated. There is generally obtained, from the mycobacteria oligomers whose monomeric units are directly derived from disaccharides and tetrasaccharides such as have just been defined.

From *Escherichia coli* are obtained disaccharides or tetrasaccharides having the formulae I to IX, preferably I to VII, in which the acyl units are acetyl units, the carboxylic groups of the D-glutamic acids are free and the meso-α-ε-diaminopimelic acid units comprise a carboxylic group free or included in a peptide linkage, the other being free. It is also possible to obtain oligomers whose monomeric units are directly derived from disaccharides and tetrasaccharides, such as have just been described.

By way of example such adjuvant agents are obtained:

either from the above-mentioned "second peak", obtained from *Mycobacterium smegmatis* (or from the second Sephadex filtration peak of the soluble fraction obtained by the action of lysozyme on *Mycobacterium smegmatis* cells delipidated under the conditions described in the first application for a French certificate of addition No. 72 22120 of June 19, 1972) by chromatography on DEAE-cellulose, by treatment preferably carried out by muramyl-L-alanine amidase of the main peak of the effluent from this chromatography, then by filtration on a molecular sieve, for instance that denoted by the name Sephadex G25, and recovery of the filtration peaks containing the adjuvant agents according to the invention;

or by acid hydrolysis carried out on the soluble agents resulting from treatment by a murolytic enzyme, for instance lysozyme, of the material derived from the whole delipidated walls of mycobacteria or of Nocardia under the conditions which have been described in the French patent application No. 71 41610 identified above, or of complete mycobacteria cells previously delipidated under the conditions described in the first French certificate of addition application No. 72 22120 filed June 19, 1972, from insoluble peptidoglycans of *E. Coli,* prepared for example by the method of Pelzer (Pelzer H., Arch. für Mikrobiol., 50 (1965) 334), by treatment of these peptidoglycans with a murolytic enzyme such as lysozyme, filtration of the solubilised fraction obtained on molecular sieve, for example that marketed under the name Sephadex G50, and recovery of the filtration peaks.

In the examples of adjuvant agents which have been described, the various aminoacids of the peptide chain may be replaced by other aminoacids which have been defined above.

For example the meso-DAP may be replaced by lysine or a fragment of a peptide chain containing lysine, which results from the example relating to the production of a peptidoglycane of *Micrococcus roseus,* which it does not contain meso-DAP, but which possesses however a considerable adjuvant activity.

Also included within the scope of the invention are the polysaccharides-polypeptides corresponding to fragments of peptidoglycanes also active which may be obtained from certain procaryotic bacteria, of which certain of the aminoacids are distinct from those of the peptidoglycanes of mycobacterial origin, for instance those in which the first aminoacid of the peptide chain is constituted by serine or glycine. Ut is the same for polysaccharides-polypeptides in which one of the aminoacids may be replaced by an equivalent aminoacid. Such as for example the case, when the glutamic acid of the peptide chain is replaced by aspartic acid.

A second group of preferred adjuvant agents is formed by those which do not contain N-acetylglucosamine. They are constituted by an N-acyl-muramic acid unit to which is linked a short peptide chain containing at least two aminoacids, for example formed from 2 to 5 aminoacids and in which the first aminoacid fixed on the carboxyl group of the N-acyl-muramic acid is constituted by alanine, serine or glycine, and the second aminoacid of said chain is constituted by glutamic acid or aspartic acid, each of the carboxyl functions of this second aminoacid being either free, or amidated (in the case of chains only including two aminoacids), or included in a linkage with another aminoacid in the case of a longer peptide chain.

Preferably, the first aminoacid is L-alanine, and the second D-glutamic acid. When the latter is amidated, it is preferably on the α carboxyl. It can be in its L form or in its D form. It may also be replaced by aspartic acid, whose chemical structure is very close to that of glutamic acid.

The possible substitution by an additional aminoacid is preferably effected on the γ carboxyl of glutamic acid (or of aspartic acid). The additional aminoacid may be any one. The third additional aminoacids are meso-α-ε-diaminopimelic acid, lysine, γ-aminobutyric acid and β-hydroxy-diaminopimelic acid.

Advantageously, the acyl group of N-acyl-Mur acid is constituted by an acetyl group. It may however also be different, for example form a glycolyl group.

The invention relates also to a method for manufacturing peptidoglycine fragments of the type concerned, which method consists of reacting N-acyl-muramic acid, whose free —OH functions, with the exception of those of the propionyl group of the muramic acid, have been previously protected, with the corresponding peptide whose free OH functions have also been previously protected.

Other features of the invention will appear also in the course of the description which follows of preferred examples of adjuvants according to the invention.

EXAMPLE I

Cells of *Mycobacterium smegmatis*, of which a strain has been deposited in the "American Type Culture Collection" under No. ATCC NBR 21732, were cultivated in Roux bottles on Sauton medium for about 12 days at 37° C. They are harvested by filtration on filter paper, washed with distilled water and stored at −20° C. until use.

100 g of cells are suspended in 500 ml of wa distilled water by cold mixing in a Waring blender, which has been precooled, until the suspension becomes homogeneous. The cells are then disrupted in a precooled French press, operated in a cold room under 420 kg/cm$^2$ pressure. After a first pass, there is added 1 mg of DNAse to reduce viscosity, following which the suspension is passed a second time through the French press. In addition to the disintegration of the cells by mechanical pressure, the cells may also be disrupted by sonic vibration of 30 ml of suspension for 25 minutes (5 times 5 minutes) in a Raytheon sonic oscillator previously cooled and operated at 10 kc/sec, as well as by disrupting the cells by means of freezing-thawing, by treatment with a zeolite, by shaking them together with glass balls, or by any other conventional means used for the disruption of mycrobial cells.

The resulting suspension is centrifuged 3 times for 15 minutes at 800 g in a refrigerated centrifuge. The pellets, constituted by non-disrupted cells, are discarded. The ultimate supernatant liquor is centrifuged for one hour at 27,500 g; the pellets of cell wall materials obtained are resuspended in 750 ml of sodium phosphate buffer (0.066 M, pH 7.8) having added thereto 125 mg trypsine, 125 mg chymotrypsine, and a small amount of an antiseptic agent such as toluene, to preclude any bacterial contamination. The product is kept over night at ordinary room temperature with magnetic stirring in an incubator and then the mixture is centrifuged for an hour at 27,500 g. The pellets of cell wall materials are washed by resuspending them and centrifuging three times with cold phosphate buffer and three times with cold distilled water.

The cell wall material is then delipidated at normal room temperature with neutral solvents; to this end, the said material is resuspended in about 30 volumes of solvent which is allowed to act for about one day with stirring. The cell wall material is thus delipidated three times with acetone, three times with ethanol-ether (1:1), three times with chloroform and three times with chloroform-methanol (2:1); this material is then dried with acetone. The dried delipidated cell wall material can then be preserved at ordinary ambient temperature until use.

1 g of the delipidated cell wall material thus obtained is resuspended in 250 ml of an 0.1 M ammonium acetate solution, pH 6.2; it is kept overnight in the cold with a few drops of toluene. The material is filtered on a sintered glass filter and washed with ethanol and chloroform. The thus washed cell wall material is then resuspended in 150 ml of 0.1 M ammonium acetate, pH 6.2, to which 12 mg of lysozyme and several drops of toluene are added; it is kept overnight in an incubator at 37° C. with stirring. After filtering on sintered glass, the insoluble residue is treated once more with lysozyme under the same conditions. The two filtrates are mixed, lyophilised, redissolved in water and lyophilised until removal of the ammonium acetate. Yield: about 90 mg of crude water soluble product per gram of dried delipidated cell wall material.

The water soluble crude product (500 mg) is then filtered on a column of "Sephadex G50" (height 80 cm, diameter 2.5 cm) in equilibrium with 0.1 N acetic acid.

In the following the agent contained in the "first peak" eluted from the column is designated "Substance A" and the products contained in the "second peak" eluted from the column denoted by "Substance B".

300 mg of the fraction corresponding to the "second peak" obtained under these conditions were chromatographed on a column of DE$_{32}$ (DEAE-cellulose Whatman) of 32 cm height and 2 cm diameter, the elution being carried out with a linear gradient (1.6 l in total) of pyridinium acetate going from 0.05 M of pyridine pH 7.0 to 2 M of pyridine pH 5.0.

The main peak of the effluent, hereinafter called substance BB, is then treated with muramyl-L-alanine amidase (coming from Myxobacter AL$_1$), then the hydrolysate is filtered on a column of Sephadex G25 of 80 cm height and 2.5 cm diameter equilibrated with 0.1 N acetic acid.

The three fractions obtained ($F_I$, $F_{II}$ and $F_{III}$) were adjuvants.

Analysis showed that the $F_{III}$ peak contained essentially disaccharides tri- or tetrapeptides;

the $F_{II}$ peak contained disaccharides hepta- or octa-peptides and tetrasaccharides hepta- or octa-peptides, practically with the exclusion of any other constituents, disregarding traces of protein aminoacids;

the $F_I$ peak contained oligomers of disaccharides tri- or tetra-peptides, containing for instance 3 to 6 disaccharide units. The $F_I$ peak contained in addition 3% by weight of neutral sugars.

EXAMPLE II

Extraction of an adjuvant agent of low molecular weight from "Substance A".

The lyophilised "Substance A" is redissolved in a solution of 0.1 N hydrochloric acid and the solution is kept at 60° C. for 12 hours. The solution is then concentrated in a rotary evaporator and dried. The dried product obtained is redissolved in 0.1 N acetic acid and the solution is filtered on a Sephadex G25 molecular sieve. The first peak containing the adjuvant agent is recovered, and called below "Substance G".

EXAMPLE III

Extraction of adjuvant agents from *E. coli*.

500 g of *Escherichia coli* β are suspended in 650 ml of a cold 9% sodium chloride solution. To this solution ten times its volume of cold acetone is slowly added. It is stirred for 5 hours at 0° C. then left to settle. The supernatant liquid is removed and the whitish deposit obtained centrifuged at 3000 g for 10 minutes. The centrifuged pellet is washed with acetone, recentrifuged, washed with ether and placed in a dessicator to dry.

115 g of acetonic powder are collected which are suspended in 5 liters of 0.1 N ammonium acetate solution and homogenised. 5 liters of 4% sodium dodecyl-sulfate solution are added and the solution is stirred, with a mechanical stirrer, for 20 hours at room temperature. An equal volume of distilled water is added, it is stirred and centrifuged at 27 000 g for 60 minutes. The centrifuged pellets are washed with 0.1 N ammonium acetate solution, then resuspended in 800 ml of this same solution. 16 ml of an 0.15 M magnesium sulfate solution and a of DNAse on the end of a spatula are added. It is left for 60 minutes at room temperature and centrifuged at 27 000 g for an hour. The centrifuged pellets are twice treated with DNAse and subjected to the action of 0.4% sodium dodecylsulfate for forty hours at normal temperature.

There is again centrifuging at 27 000 g, for ninety minutes. The centrifuged pellet is taken up again in 600 ml of distilled water and it is treated with an equal volume of 0.1 M phosphate buffer, pH 7.8, containing 0.02% trypsin and 0.02% chymostrypsin, for fifteen hours at 37° C. The precipitate is washed once with 0.05 M phosphate buffer, pH 7.8, and three times with distilled water, and it is lyophilised. 3 g of peptideglycane are thus obtained.

This peptidoglycane is hydrolysed by the lysozyme which solubilises it almost entirely. To do this, 20 mg of the peptidoglycane are incubated in the presence of 2 mg of lysozyme in 2 ml of 0.01 M phosphate buffer, pH 6.0 at 37° C. for fifteen hours, in the presence of toluene to avoid contamination.

The lysate is dissolved in 0.1 N acetic acid and filtered on a column of SEPHADEX G50 (h=80 cm, diameter=2.5 cm). Three peaks which contain all three constituents of the peptidoglycane are obtained: alanine, glutamic acid, meso-diaminopimelic acid, N-acetyl-glucosamine, and N-acetyl-muramic acid.

The last peak ($H_3$ peak), that which has the lowest molecular weight, is constituted from a mixture of disaccharide-tetrapeptide and disaccharide-tripeptide.

The second peak ($H_2$ peak) is constituted from tetrasaccharides hepta- and octa-peptides.

The small amount of product obtained in the first peak ($H_1$ peak) is formed from oligomers of the monomer of the third peak.

The constituents of these three peaks are adjuvants, as evidenced by pharmacological tests of granuloma, under the conditions which will be described below. The $H_3$ peak contains the most active agent.

EXAMPLE IV

Preparation of the substance of formula III in the practically pure state (muramic acid in the N-glycolylated state and glutamic acid and meso-DAP acid amidated, as indicated above for the products from mycobacteria).

This fraction is obtained by preparative elecytrophoresis of the $F_{II}$ fraction of Example I. The electrophoresis is carried out on a Whatman 3MM paper in a pyridine-acetic acid buffer, pH 3.9, over 60 cm, under a voltage of 60 volts/cm. The operation is effected under white-spirit in a Gilson apparatus. The substance migrates towards the cathode by 6 cm in one hour; under these conditions, the alanine migrates by 5 cm, and the glucosamine by 25 cm, also towards the cathode.

The substance is eluted from the paper by 0.1 N acetic acid. This substance is denoted below under the name "Substance I".

EXAMPLE V

Preparation of substance I whose formula is that described above (muramic acid in the N- glycolated state and glutamic and meso-DAP acids amidated, as indicated above for the products derived from mycobacteria).

This fraction is obtained by preparative electrophoresis of the fraction $F_{III}$ from Example I. The electrophoresis is done under the same conditions as those described in Example IV. In this case, the migration of the substance is 7 cm towards the cathode. The substance eluted is denoted below by the name "Substance J".

EXAMPLE VI

Preparation of the walls of *Micrococcus roseus*

The cells of M. roseus (strain No. 5693 of the Pasteur Institute of Paris) are cultivated on "Nutrient broth" (Difco) in Erlenmeyer flasks 2 liters capacity containing 800 ml of medium placed on a Biolafitte (Maisons-Lafitte) shaker table at 25°, and collected to ⅔ of the exponential growth phase.

The bacteria are broken up by shaking in the presence of small glass balls: in a typical experiment, 30 g of fresh bacteria are suspended in 150 ml of distilled water: 150 ml of small glass balls 0.17–0.18 mm diameter are added and the mixture placed in the 400 ml bowl of an Omnimixer (Sorvall) cooled by immersion in a bath of ice water. The mixer is put into operation at full speed for 30 minutes. After decantation of the glass balls, the supernatant liquid is preserved: the supernatant liquid derived from washing the bowls twice with 100 ml of distilled water are added to it. The combined supernatant liquids are centrifuged three times for 10 minutes at 800 g in a refrigerated centrifuge to remove the debris of the glass balls and the unbroken bacteria. The resulting supernatant liquid is centrifuged for an hour at 27,000 g in a cooled centrifuge: the pellet constituted by the walls is suspended, by means of a Potter grinder with a teflon piston, in 150 ml of 0.066 M phosphate buffer, pH 7.8, supplemented with 30 mg of trypsin and 30 mg of chymotrypsin, then incubated overnight at the temperature of the laboratory in the presence of some drops of toluene to prevent contamination. After centrifuging for an hour at 27,500 g, the pellet of the deproteinisid walls is washed by a replacing it in suspension by means of the Potter grinder with a teflon piston and centrifuging for an hour at 27,500 g at +4°, three times with 150 ml of 0.066 M phosphate buffer, pH 7.8 and three times with 150 ml of distilled water. The walls are then lyophilised: they are adjuvants as shown by Table II below.

It is known, from publications by, respectively:
(1) J. F. PETIT, E. MUNOZ and J. M. GHUYSEN, BIOCHEMISTRY, 5, 2764–2776 (1966);
(2) E. MUNOZ, J. M. GHUYSEN, M. LEYH-BOUILLE, J. F. PETIT, H. HEYMANN, E. BRICAS and P. LEFRANCIER, Biochemistry, 5, 3748–3764 (1966);

that the peptidoglycane of *M. roseus* is constituted of N-acetylglucosaminyl-β-1,4-N-acetylmuramyl-L-alanyl-D-isoglutaminyl-L-lysyl-D-alanine repeating units of which the amino-ε group of the lysine is substituted by a peptide (L-Ala)$_3$-L-Thr; the interpeptidic linkages are formed by a linkage between the terminals D-Ala of a tetrapeptide and the terminal L-Ala of the peptide (L-Ala)$_3$-L-Thr substituting lysine of another tetrapeptide (1). To prove that the adjuvant activity of the wall of *M. roseus* was connected with its peptidoglycane, a disaccharide pentapeptide was isolated therefrom by enzymatic degradation. In the foregoing, the abbreviation "Thr" denotes threonine.

EXAMPLE VII

Isolation of a disaccharide pentapeptide from the peptidoglycane of the wall of *M. roseus*.

150 mg of *M. roseus* walls were suspended in 30 ml of 0.05 M veronal buffer, pH 8.6 and supplemented with 20 ml of a preparation of S.a.endopeptidase of *Streptomyces albus* G obtained by the method of GHUYSEN (J. M. GHUYSEN, L. DIERICKX, J. COYETTE, M. LEYH-BOUILLE, M. GUINAND and J. N. CAMPBELL, biochemistry, 8, 213–222 (1969)), then incubated overnight at 37° in the presence of some drops of toluene. To the incubation mixture is then added 0.2 M ammonium acetate up to a 0.2 M concentration and the pH adjusted to 6.2 with acetic acid. 3 mg of lysozyme of chicken egg-white (Sigma) is then added and the mixture incubated at twenty-four hours at 37°. 2% of pronase and calcium acetate is then added up to a 0.01 M concentration and the solution kept at 37° for forty-eight hours. After concentration to 15 ml in a rotary evaporator, the lysate is filtered on a column of SEPHADEX G25 (h=80 cm, diameter=2.5 cm) equilibrated with 0.1 M acetic acid. The recording of the optical density of the effluent at 206 nm enables it to be divided into four fractions; the analyses carried out have shown that the second fraction was constituted from glucosamine, muramic acid, alanine, glutamic acid, lysine and threonine in the molar ratios (1:1:2:1:1). The Morgan Elson reaction having shown that the amino sugars were present in the form of disaccharides, the formula of the compound, in view of its method of preparation, is as follows:

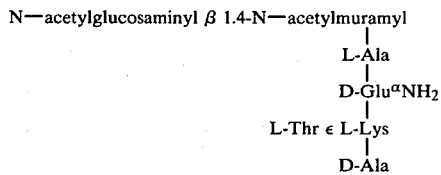

This disaccharide pentapeptide is an adjuvant as is shown in Table II.

EXAMPLE VIII

Preparation of N-acetylmuramyl-L-alanyl-D-isoglutamyl-meso-DAP

Cells of *Bacillus cereus* T were cultivated on Antibiotic Medium 3 (Difco) in Erlenmeyer flasks of 2 liters containing 800 ml of medium and shaken on a Biolafitte shaker table. At two-thirds of the exponential growth phase, 50 μug/ml of D-cycloserine (Roche) was added to the culture; after a half-hour at 37° under the same conditions of shaking, the culture, whose optical density ceased to increase after the addition of the D-cycloserine, was centrifuged. The pellet of cells was extracted with 4% cold trichloracetic acid: typically for 15 g of cells weighed fresh, 100 ml of trichloracetic acid (TCA) were used. The suspension of cells in the TCA was homogenised in a Potter grinder with a teflon piston, then centrifuged for an hour at 27,500 g at +4°; the supernatant was extracted with ether several times so as to remove the trichloracetic acid and neutralised by NH$_4$CH, then concentrated to 10 ml in a rotary evaporator. The UDP-N-acetylmuramyltripeptide, of which the D-cycloserine causes the accumulation in the cell (according to K. IZAKI, M. MATSUHASHI and J. L. STROMINGER, J. Biol. Chem., 243, 3180–3192 (1968) is found in this concentrated extract which has been filtered on a column of SEPHADEX G25 (h=80 cm, diameter=2.5 cm) equilibrated with 0.02 M ammonium acetate. The recording of the optical density of the effluent at 260 nm enables it to be divided into four fractions. The third which contains the product sought was purified by chromatography on 3 MM WHATMAN paper for three days in the solvent ethanol-M ammonium acetate, pH 7.5 (5:2); the principal absorption band in the ultraviolet was eluted, then hydrolysed in 0.02 N HCl at 100° for twenty minutes to hydrolyse the linkage between the nucleotide and the muramyltripeptide sought. After lyophilisation, the hydrolysate was subjected to electrophoresis for two hours at pH 4, at 4 v/cm on 3 MM WHATMAN paper, under varsol (white-spirit) in a GILSON apparatus (GILSON MEDICAL ELECTRONICS, VILLIERS-LE-BEL). After development with ninhydrinecollidine, the principal band was eluted, lyophilised and analysed. It corresponds well to the product sought. 1 mg was obtained from 8 liters of *B.cereus* culture poisoned with D-cycloserine; this product is an adjuvant as shown in Table II.

EXAMPLE IX

In the following is described the chemical synthesis of the adjuvant substances according to the invention, more particularly of the N-acetyl-muramic acid molecules on which are respectively fixed di-, tri- and tetrapeptidic chains.

However there will first be described the synthesis of the di-, tri- and tetra-peptides of the type concerned, before their respective coupling on the N-acetyl-muramic acid.

A: Synthesis of peptidic chains

Below are described the syntheses:

of the hydrochloride of the benzylic ester of L-alanyl-D-isoglutamine:

-L-Ala-D-Glu-α-NH$_2$, HCl.

of the hydrochloride of benzylic ester of [L-alanyl-D-isoglutaminyl]. (L), Z-(D)meso-diaminopimelyl-(L). [D-alanine], (D)-amide:

[L-Ala-D-Glu-α-NH$_2$]-(L)-, Z-(D)-m-DAP-(L) (O-Ala-OBzl), (D)-NH$_2$, HCl.

of the hydrochloride of the benzylic ester of [L-alanyl-D-isoglutominyl]-(L), Z-(D)-meso-diaminopimelyl-(D) amide:

-[L-ala-D-Glu-α-NH$_2$]-(L), Z-(D)-m-DAP-(L)-[OBzl], (D)-NH$_2$, HCl.

The abbreviations used are:

Z for benzyloxycarbonyl

BOC for t-butyloxycarbonyl m DAP for meso-αα'diaminopimelic acid

OSu for succinimidic ester.

The melting points were determined in capillary tubes with the apparatus of Dr. TOTTOLI (Ets BUCHI FLAWIL-SUISSE) and were not corrected. The measurements of the physical constants and the elementary analyses were carried out on products dried under vacuum ($10^{-2}$ mm Hg) generally for twenty hours at 78°. The elementary analyses were carried out with a PERKIN-ELMER automatic CHN micro-analysis apparatus. The rotatory powers were determined by means of the ROUSSEL-JOUAN electronic polarimeter. The chromatographs were done on fine plates of silica gel (MERCK) in the mixture of solvents (A): n-butanol-pyridine acetic acid-water (30-20-6-24 v/v) or (B): chloroform-methanol-ammonia (2-2-1 v/v).

(a) Diamide of BOC, Z-meso-diaminopimelic acid [BOC, Z-m-DAP-$(NH_2)_2$]

6.12 g (7.80 mmoles of the dicyclohexylammonium salt of BOC, Z-meso-diaminopimelic acid (prepared according to the methods of DEZELEE, P. and BRICAS, E. Biochem. 1970, 9, (823) and of DEZELEE, P. and BRICAS E. in "Peptides 1969: Proceedings of the Tenth European Peptide Symposium" (E. SCOFFONC, Ed) p. 347–355 North Holland, Amsterdam) were desalted by a solution of 4 N HCl in tetrahydrofurane. The oily residue obtained is taken up in 25 ml of tetrahydrofurane and the solution cooled to −10°. 4.05 ml (15.6 mmoles) of isobutyl chlorocarbonate, then 2.2 ml (15.6 mmoles) of triethylamine were added. After ten minutes, a current of dry ammonia was bubbled through the solution for thirty minutes at room temperature. A very abundant white precipitate formed and was taken up, after distillation of the tetrahydrofurane, in a mixture of ethyl acetate (60 ml) and water (20 ml). The organic solution was then washed twice with a 1 M solution of $NaHCO_3$ (20 ml each time), then with distilled water until neutrality. It was then dried over $MgSO_4$, and finally concentrated to dryness. The solid residue obtained was crystallized in the mixture ethyl acetate-hexane: 2.06 (Yield 63%). M.P.$_c$ 169°–172°. Elementary analysis ($C_{20}H_{30}O_6N_4$, 422.49). Calculated C% 56.9. H% 7.2. N% 13.3. Found C% 56.8. H% 7.5. N% 13.5.

(b) Hydrochloride of the diamide of Z-meso-diaminopimelic acid [Z-m-DAP-$(NH_2)_2$, HCl]

1.86 g (4.4 mmoles) of the diamine of BOC, Z-meso-diaminopimelic acid were dissolved in 14 ml of a 1 N HCl solution in acetic acid. After thirty minutes at 25°, the solution was concentrated to dryness and the residue dried in a dessicator, in the presence of soda. The product was finally crystallised in the mixture methanol-ether: 1.5 g (Yield 90.5%). M.P.$_c$ 138°–140°. Rf A° 0.7).

(c) Hydrochloride of Z-(D)-meso-diaminopimelic-(D)-monoamide Z-(D)-m-DAP-$NH_2$, HCl This product was prepared according to the method prefected by DEZELEE and BRICAS (LEFRANCIER, P. and BRICAS, E. Bull. Soc. Chim. Biol., 1967, 49, 1257) to obtain BOC-(D)-meso-diaminopimelic-(D)-monobutyloxycarbonylhydrazide BOC-(D)-m-DAP-(D)-NH-NH-BOC.

A solution of 1.144 g of hydrochloride of the diamide of Z-meso-diaminopimelic acid (3.2 mmoles), in 100 ml of distilled water was adjusted to pH 8.6 with a solution of N KOH, and kept at 37°. There were added 3 ml of a solution of leucine aminopeptide previously activated (0.8 ml of a solution of LAP containing 2 mg of protein per ml, 0.7 ml of distilled water, 1.5 ml of a TRIS buffer pH 8.5, 0.5 M, 3 ml of an 0.025 M solution of $MgSO_4$. 90 min at 37°). The pH of the solution is kept at 8.6 by addition of an 0.1 N solution of $H_2SO_4$ by means of a pH-Stat. After about one night, a light precipitate was filtered, and the filtrate acidified with a 2 N HCl solution, then concentrated to a small volume. The precipitate obtained was filtered after one night at 0°: 400 mg (Yield 70%). The filtrate was concentrated to 4 ml and passed over a column of SE-SEPHADEX ($NH_4^+$), (2×20 cm) pre-equilibrated with a 1 M acetic acid solution. The Z-(D)-m-DAP-(D)-$NH_2$ was eluted with an 0.1 M solution of ammonium acetate in 1 M acetic acid. By lyophilisation, 100 mg was obtained.

The two batches were recrystallised in an ethanol-ether mixture: 480 mg (Yield 84%). MP$_c$ 245°–250°. $[\alpha]_D^{25} = 5°$ (c=0.5 N HCl). Rf (A) 0.65.

(d) Succinimide ester of BOC-L-alanyl-D-isoglutamine (BOC-L-Ala-D-Glu(OSu)-$NH_2$)

To a solution in 30 ml of dimethylformamide of 4.05 g (10 mmoles) of BOC-L-alanyl-D-isoglutamine (2), were added 1.15 g of N-Hydroxy-succinimide (10 mmoles) and 2.26 g dicyclohexylcarbodiimide (11 moles). After one night at ordinary temperature, the dicyclohexylurea was filtered and the filtrate concentrated to dryness. The product was crystallized in a isopropyl alcohol-diisopropylether mixture: 4 g (Yield 100%). MPc 69°–70° (with decomposition). $[\alpha]_D^{25} = 12.2°$ (c=1 dioxane).

This product seems to be decomposed fairly rapidly. It is kept in the dessicator in the presence of $P_2O_5$, or preferably prepared just before use.

(e) Hydrochloride of the benzylic ester of L-alanyl-D-isoglutamine 1 g (2.5 mmoles) of the benzylic ester of the BOC-L-alanyl-D-isoglutamine (2), are dissolved in 30 ml of an N HCl solution in acetic acid. After 30 min, the solution is concentrated to dryness and the residue is taken up in a minimum amount of methanol. The product is precipitated with ether: 800 mg (Yield 94%). MPc 153°–157°. $[\alpha]_D^{25} = +8.1°$ (c=1 Methanol).

An elementary analysis ($C_{15}H_{22}O_4N_4Cl$, 342.87. Calculated C% 52.5. H% 6.5. N% 12.3. Found C% 53.5. H% 6.4. N% 12.2

(f) [BOC-L-alanyl-D-isoglutaminyl]-(L), Z-(D)-meso-DAP-(D)-$NH_2$ 1.18 g (3.3 mmoles) of the hydrochloride of the monoamide (D) of Z-(D)-meso-diaminopimelic acid were dissolved in 5 ml of distilled water. There were added, at 0°, 0.72 ml (6.6 mmoles) of N-methylmorpholine, then a solution in 15 ml of dimethylformamdie of 1.2 g (3 mmoles) of the succinimic ester of BOC-L-alanyl-D-isoglutamine. The precipitate observed at the beginning of the reaction solubilises after two hours. After forty-eight hours, the reaction mixture is concentrated to dryness and taken up again in 50 ml of n-butyl alcohol, previously equilibrated with a solution of 1 M acetic acid, and 20 ml of a solution of 1 M acetic acid, previously equilibrated with n-butyl alcohol. The n-butanol phase is extracted five times with small amounts of acetic acid solution. The combined aqueous phases were washed three times with 10 ml of n-butyl alcohol. The organic phases were finally combined and concentrated almost to dryness. By the addition of ether, a precipitate is obtained (1.8 g); it is taken up again in absolute ethanol. The insoluble material observed is filtered, and the filtrate concentrated to the minimum. By precipitation with ether, there was obtained 1.6 g (Yield 80%). MPc softening 10°–110°, melting 115°. $[\alpha]_D^{25} = -5°$ (c=1 Methanol). Elementary analysis ($C_{28}H_{42}O_{10}N_6$, 623.09). Calculated C% 54.0. H% 6.8. N% 13.5. Found C% 54.1. H% 6.7. N% 13.5.

(g) [BOC-L-Ala-D-Glu-α-$NH_2$]-(L), Z-(D)-meso-DAP-(L)-D-Ala-OBzl, (D) $NH_2$ 570 mg (0.92 mmoles) of [BOC-Ala-D-Glu-α-$NH_2$]-(L), Z-(D)-meso-DAP-(D)-$NH_2$ were dissolved in 30 ml of tetrahydrofurane. At −15° were added 0.26 ml (1 mmole) of of isobutyl chlorocarbonate and 0.11 ml (1 mmole) of N-methylmorpholine. After 10 min, there were added in solution in 10 ml of tetrahydrofurane 352 mg (1 mmole) of p-toluene sulfonate of the benzylic ester of D-alanine and 0.11 ml (1 mmole) of N-methylmorpholine. At ordinary temperature, at the end of an hour, a solvated precipitate was obtained. The reaction was continued for twenty-four hours. After concentration to dryness, the residue was taken up again in 25 ml of ethyl acetate and 10 ml of distilled water. The organic phase was washed successively with a 10% citric acid solution, with distilled water with a 1 M, $NaHCO_3$ solution, then with distilled water until neutral pH. The ethyl acetate phase was concentrated and the residue obtained dry in a dessicator in the presence of $P_2O_5$. The product was crystallised in an ethyl acetate-petrolium ether mixture: 400 mg (Yield 55%). MPc with softening 180°, melting 215°. (The rotatory power of a methanol solution (c=1) is too low to be taken into consideration).

Elementary analysis ($C_{38}H_{53}O_{11}N_7$, 783.89). Calculated C% 58.2. H% 6.8. N% 12.5. Found C% 58.0. H% 6.7. N% 12.55.

(h) Hydrochloride of [L-Ala-D-Glu-α-$NH_2$] (L), Z-(D)-meso-DAP-(L) [L-Ala-OBzl]; (D)-$NH_2$ 850 mg (1.1 mmoles) of BOC-L-Ala-D-Glu-α-$NH_2$ (L), Z-(D)DAP-(L)-L-Ala-OBzl, (D)-$NH_2$, were dissolved in 5 ml of an N HCl solution in acetic acid. After 30 min at 25° the solution was concentrated to dryness, and the residue crystallised in a methanol-ether mixture: 750 mg (Yield 95%). MPc 90°–100° (not distinct). $[\alpha]_D^{25} = +3.5°$ (c=0.5 methanol).

Elementary analysis ($C_{33}H_{46}O_9N_7Cl$, HCl 0.25 $H_2O$). Calculated C% 52.2. H% 6.3. N% 12.9. Found C% 52.26. H% 6.14. N% 12.69.

Aminoacid analysis of a total hydrolysate (effected in a tube sealed under vacuum, at 100° for 24 hours, in the presence of 6 N HCl) of 0.5 mg of the derivative gives Ala 1.9; Glu 1; DAP 1.

(i) Hydrochloride of the benzyl ester of Z-(D)-mesodiaminopimelyl-(D)-monoamide

Z-(D)-m-DAP-(L)-OBzl, (D)-$NH_2$, HCl

The di-Z-meso-diaminopimelyl-(D)-monoamide was prepared by the method described by Van Heijenhoort J., Bricas E., Nicot C. (Bull. Soc. Chim. 1969 8 2743).

4.57 g (10 mmoles) of this derivative was suspended in 50 ml of anhydrous ether. There were added in 30 min, at 0°, and with stirring, 10 mmoles of finely powdered phosphorous pentachloride. After complete solution of the phosphorous pentachloride, the reaction mixture was filtered and the filtrate was concentrated to dryness under vacuum at 40°. Concentration after the addition of fresh solvent was repeated several times. The residue was then taken up again in 10 ml of benzyl alcohol and the solution poured at 0° into a flask containing 50 ml of ether previously saturated with HCl. The temperature was allowed to reach 25°, the solution being stirred; carbon dioxide escapes, whilst a precipitate is formed. It is left overnight, then the precipitate is filtered and washed with ether. The product (i) identified above is thus obtained.

(j) [BOC-L-Ala-Glu-α-$NH_2$]-(L), Z-(D)-m-DAP-(L)-OBzl, -(D)-$NH_2$ 500 mg (2 mmoles) of the hydrochloride of the benzyl ester of Z-(D)-meso-diaminopimelyl-(D)-monoamide were dissolved in 10 ml of dimethylformamide. At 0° there were added 0.22 ml (2 mmoles) of N-methylmorpholine, then a solution in 10 ml of dimethylformamide of 800 mg (2 mmoles) of the succinimidic ester of BOC-L-alanyl-D-isoglutamine.

After forty-eight hours, the reaction mixture was concentrated to dryness and taken up again in 50 ml of n-butyl alcohol, previously equilibrated with 1 M acetic acid solution, and 20 ml of 1 M acetic acid, previously equilibrated with N-butyl alcohol. The n-butanol phase was extracted five times with small amounts of the acetic acid solution. The combined aqueous phases were washed three times with 10 ml butyl alcohol. The organic phases were finally combined and concentrated to dryness.

The product (j) identified above was obtained by precipitation with ether.

(k) Hydrochloride of [L-Ala-D-Glu-α-$NH_2$] (L), Z-(D)-meso-DAP-(L)-OBzl, (D)-$NH_2$ 712 mg (1 mmole) of BOC-L-Ala-D-Glu-α-$NH_2$(L), Z-(D)-m-DAP-(L) OBzl, (D)-NH were dissolved in 5 ml of an HCl solution in acetic acid. After 30 min at 25° the solution was concentrated to dryness and the residue taken up in methanol and precipitated with ether: 600 mg (98%).

Analysis of aminoacids of a total acid hydrolysate (carried out in a tube sealed under vacuum at 110° for 24 hours in the presence of 6 N HCl), of 0.5 mg of the derivative gave Ala 0.95-Glu 1-DAP 0.90.

B: Total synthesis of the glycopeptide 2-(2-acetamido-2-Desoxy-3-O-D-glucopyranosyl)-D-propionyl-L-Ala-(γ-CH)-D-α-Glu $NH_2$.

The reactions utilised are indicated in Table I below.

In Table I there are used the abbreviations "Ph" for the phenyl groups and "Ac" for the acetyl groups.

TABLE I

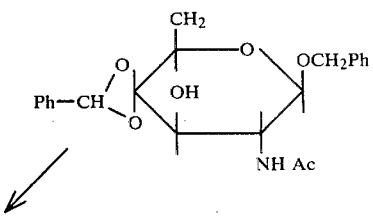

(A)

TABLE I-continued

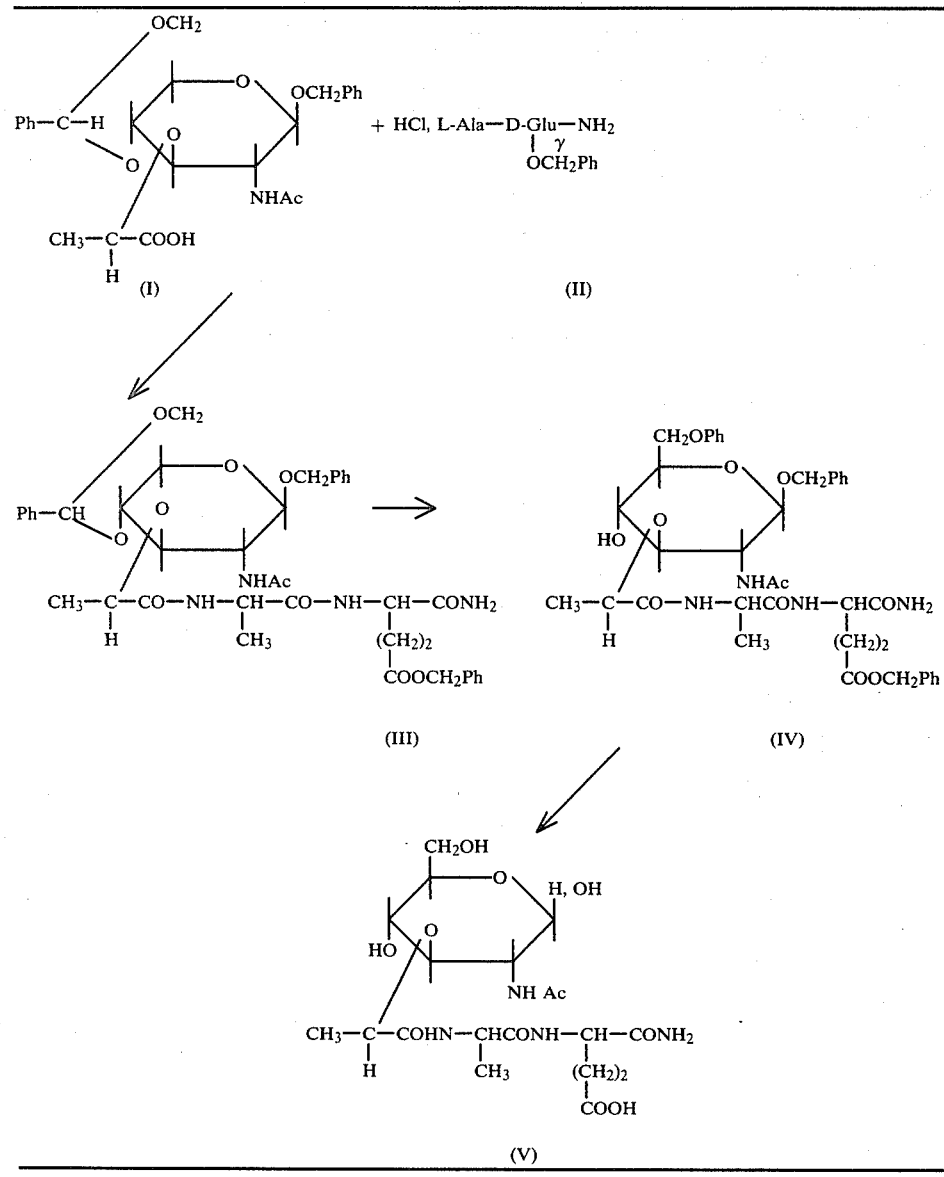

(a) Preparation of benzyl-2-acetamido-4.6-O-benzylidene-2-deoxy-β-D-glucopyranoside (compond A of Table I)

It is prepared starting from benzyl-2-acetamide-3.4,6,-tri-O-acetyl-2-desoxy-β-D-glucopyranoside, which is deacetylated by sodium methanolate, then protected by a 4,6-O-benzylidene according to the method of P. H. GROSS and R. W. JEANLOS, J. Org. Chem. 32 (1967), 2759.

(b) Preparation of benzyl-2-acetamido-4.6-O-benzylidene-3-O-(D-1-carboxyethyl)-2-desoxy-β-D-glucopyranoside (I)

4 g of benzyl-2-acetamido-4.6-O-benzylidene-2-desoxy-β-D-glucopyranoside A were dissolved at 90° in anhydrous and deperoxidised dioxane (450 ml). After the addition of a 50% suspension of sodium hydride in oil (2.80 g of suspension), the whole is shaken for 2 hours at 90°. L-α-chloropropionic acid (1.840 g) is then added. A second addition of sodium hydride (2.80 g of suspension) is made 3 hours after the addtion of the acid. The mixture is then left overnight at 65°–67°, with mechanical stirring. After cooling in an ice bath, the excess sodium hydride is carefully destroyed by the addition of water (110 ml). The mixture separates into two phases. The lower phase is removed; the upper phase is separated, filtered and evaporated under vacuum. The residue is diluted with water (250 ml), the aqueous solution obtained being washed with chloroform. This aqueous solution is then cooled to 0° C. and 2.5 M hydrochloric acid added, to a pH of 3. The compound (I) precipitates and is immediately drained and washed carefully with cold water. After crystallisation in methanol, (I) is obtained in the pure state (3.64 g, 76%), m.p. 264°–265° $[\alpha]_D^{20} -52°$ (c 0.41 ethanol); spectrum i.r.:$\nu_{max}^{Nujol}$ 3.320 (NH), 3,080 (Ph), 1,760 (COOH), 1,660 (Amide I), 1,565 (Amide II), 740 and ν 695 cm$^{-1}$(Ph).

(c) Preparation of the glycopeptide 2-(2-acetamide-2-desoxy-3-O-D-glucopyranosyl)-D-propionyl-L-Ala-(γ-OH)-D-α-GluNH₂

The general principle of the preparation is as follows:

Benzyl-2-acetamido-4.6-O-benzylidene-3-O-(D-1-carboxyethyl)-2-desoxy-β-D-glucopyranoside[4] (I) is condensed with the hydrochloride of L-Ala-(γ-O-benzyl)-D-Glu NH$_2$ according to the method of Woodward et al (Tetrahedron, Suppl. 8 (1966) 321). The solvent used is a mixture of N-N-dimethylformamide and acetonitrile 1:2 (v:v). 2-(benzyl-2-acetamido-4.6-O-benzylidene-2-desoxy-3-O-β-D-glucopyranosyl)-D-propionyl-L-Ala-(γ-O-benzyl)-D-α-Glu NH$_2$ (III) is thus obtained in the crystalline state with a yield of more than 80%. The reactant K of Woodward (N-ethyl-5-phenylisoxazolium-3'-sulfonate) was chosen since it results in practically no racemisation and gives very good results with glutamine type amides, including in N-N-dimethylformamide; the only drawback of the latter solvent is that it leads to a lower yield, which is not the case here by using a mixture acetonitrile-N-N-dimethylformamide. Treatment of the glycopeptide protected (III) with 60% of acetic acid gives the 2-(benzyl-2-acetamido-2-desoxy-3-O-β-D-glucopyranosyl)-D-propionyl-L-Ala-(γ-O-benzyl)-D-α-Glu NH$_2$ (IV) in the crystalline state, with a yield of the order of 70%. The glycopeptide sought (V) is obtained by catalytic hydrogenation of the compound (IV) in glacial acetic acid, in the presence of palladiated carbon. It has not been obtainable in the crystalline state and its very high hygroscopicity has failed to lead to a very satisfactory elementary analysis. It is homogeneous in chromatography on a thin layer of silica gel (propanol-water, 7:3, v/v), as well as on paper (n-butanolacetic acid-water, 5:1:2, v/v/v).

These operations were carried out under the experimental conditions described below.

General conditions

The melting points were measured in a capillary tube by means of a Büchi apparatus and are not corrected. The rotatory powers were determined by means of a Perkin-Elmer (Model 141) polarimeter. The infrared spectra were recorded on a Jouan Jacco IRA-1 spectrophotometer. The homogeneity of the compounds prepared were checked by chromatography on glass plates coated with Merck HF 254 silica gel (thickness 0.25 mm) and developed by vaporisation of an alcoholic solution with 50% concentrated sulfuric acid and heating by means of an epiradiator. Chromatography on a column was carried out by means of Merck silica gel (0.063–0.200 mm). Chromatography on paper were down flow and carried out on Whatmann No. 1 paper. Elementary analyses were carried out by the Central Service of Micro-Analysis of the Centre National de la Recherche Scientifique (Thiais).

2-(benzyl-2-acetamido-4.6-O-benzylidene-2-desoxy-3-O-β-D-glucopyranosyl)-D-propionyl-L-Ala-(γ-O-benzyl)-D-α-Glu NH$_2$ (III)

A solution of 157 mg benzyl-2-acetamido-4.6-O-benzylidene-3-O-(D-1-carboxyethyl)-2-desoxy-β-D-glucopyranoside (I), (0.33 mole) in the mixture acetonitrile-N-N-dimethylformamide (2:1, V/v, 5 ml) containing one equivalent (0.33 mmole) of triethylamine is poured into a suspension, kept at 0°, of N-ethyl-5-phenylisoxazolium-3'-sulfonate (84.3 mg) Aldrich (Woodward's reactant K) in acetonitrile (5 ml). The mixture is shaken at 0° C. until a limpid solution is obtained (about 1 h.30). A solution of the hydrochloride of L-Ala-(γ-O-benzyl)-D-α-Glu Nh$_2$ (II) (114.4 mg, 0.33 mmole) in the mixture acetonitrile-N-N-dimethylformamide (2:1, v/v, 5 ml) containing one equivalent (0.33 mmole) of triethylamine is then added. After stirring overnight at ambient temperature the solvents were evaporated under vacuum, the solid residue obtained being carefully extracted with warm water, in order to remove the secondary products. The solid is strained, dried and crystallised in ethanol, giving III (208 mg, 82%), m.p. 243°–245°, [α]$_D^{20}$ −20° (c 0.5, N-N-dimethylformamide, infrared spectrum: $\nu_{max}^{Nujol}$ 3,440, 3,320 (NH), 3,080, 3,060 (Ph), 1,740 (ester), 1,645 (Amide I), 1,540 (Amide II), 740 and 690 cm$^{-1}$(Ph).

Anal. Calc. for C$_{40}$H$_{48}$N$_4$O$_{11}$: C, 63, 15; H, 6,36; N, 7.36. Found: C, 62,96; H, 6,22; N, 7,49.

2-(benzyl-2-acetamido-2-desoxy-3-O-β-D-glucopyranosyl)-D-propionyl-L-Ala-(γ-O-benzyl)-D-α-Clu NH$_2$ (IV)

The compound (III) (200 ml) is suspended in 60% acetic acid (15 ml) and heated for 1 hour at 100°. After cooling the solution, the acetic acid is evaporated under vacuum, the last traces of acid being removed by the addition of water followed by evaporations, the traces of water being finally eliminated by codistillation in the presence of toluene. The residue obtained is chromatographed on a column of silica gel (15 g) (chloroform-methanol, 85:15, v/v). The pure fractions are combined, evaporated under vacuum, giving a chromatographically pure residue of the compound (IV) (129 mg, 73%), which is crystallised in a mixture of tetrahydrofurane-petrolium ether (11(mg, 65%), m.p. 217°–219°, [α]$_D^{20}$ −1° (c 0.45, N-N-dimethylformamide); infrared spectrum: $\nu_{max}^{Nujol}$ 3,450–3,230 (OH,NH), 1,740 (ester), 1,645 (Amide I, wide band), 1,545 (Amide II), 720 and 690 cm$^{-1}$ (Ph).

Anal. Calc. for C$_{33}$H$_{44}$N$_4$O$_{11}$: C, 58,92; H, 6,59; N, 8,32. Found: C, 58,78, H, 6,50; N, 8,25.

2-(2-acetamido-2-desoxy-3-O-D-glucopyranosyl)-D-propionyl-L-Ala-(γ-OH)-D-α-Glu NH$_2$ (V)

The compound (IV) (69 mg) is catalytically hydrogenated in glacial acetic acid (10 ml), in the presence of palladium on carbon (25 mg). At the end of three hours, the catalyst is drained and the filtrate evaporated under vacuum. The compound (V) is then obtained in the form of a very hydroscopic glass which it has not been possible to crystallise.

This compound is homogeneous after chromatography on a thin layer of silica gel (n-propanol-water, 7:3, v/v), as well as after chromatography on paper (n-butanol-acetic acid-water, 5:1:2, v/v/v): R$_f$=0.30, development being done by means of the Sharon reactant (J. Biol. Chem., 239 (1964) PC 2398) and by means of silver nitrate according to TREVELYAN et al. (Nature, 166, (1950) 444). This confirms the hydrogenolysis of the glycosidic function. /

A test carried out on a very small amount shows complete and immediate activity with an etherial solution of diazomethane, indicating the presence of a free carboxylic acid.

After hydrolysis, the only titratable constituent in an aminoacid analyser are alanine, glutamic acid and muramic acid.

The compound finally obtained (Mur-N-Ac-Ala-GluNH$_2$) was tested for its adjuvant activity.

The same operational procedure enables, starting from the compound I, the preparation of the N-acetyl muramic dipeptide and tripeptide derivatives, by using, instead of the hydrochloride of the benzyl ester of L-alanyl-D-isoglutamine (compound II of Table I, also referred to above under e), respectively the hydrochloride of the benzyl ester of [L-Alanyl-D-isoglutaminyl]-(L), Z-(D)-meso-diaminopimelyl-(D) amide (compound k) and the hydrochloride of the benzyl ester of [L-alanyl-D-isoglutaminyl]. (L), Z-(D)-meso-diminopimelyl-(L). [D-Alanine], (D)-amide compound h.

Pharmacological properties of the agents according to the invention

The agents according to the invention show a powerful adjuvant activity and are free of serious drawbacks which have limited the therapeutic use of mycobacteria and the Greund adjuvant. These very favourable characteristics were established by the pharmacological tests described below.

"Substance BB" denotes that contained in the principal elution peak from DEAE cellulose of Example I.

Substances $F_I$, $F_{II}$ and $F_{III}$ correspond to the fractions contained in peaks $F_I$, $F_{II}$ and $F_{III}$ of Example I.

Substance G is that obtained in Example II.

The substances $H_I$, $H_{II}$ and $H_{III}$ come from peaks $H_1$, $H_2$ and $H_3$ of Example III.

I. Demonstration of the adjuvant properties of the agents according to the invention.

Female Hartley guinea-pigs of 300–350 g received, in the plantar pad of each of the two rear paws, an emulsion compound of equal parts of incomplete Freund adjuvant and a physiological solution containing ovalbumin (5 mg/guinea-pig) and the preparation to be tested. The incomplete Freund adjuvant (FIA) (that is to say not containing myco-bacteria), is the complete adjuvant (FCA) marketed by the DIFCO company were used as controls.

The rates of antibodies with respect to ovalbumin were determined three weeks after injection. The antibody rate is expressed in μg/ml of serum of the antigen-antibody precipitate at the point of equivalents.

The granuloma (indicated by the sign + in Table No. 1 below) was observed three weeks after injection.

The delayed hypersensitivity to ovalbumin was measured by cutaneous reaction four weeks after injection; it is expressed by the diameter in millimeters of the erythema (E), of the induration (I) or the necrosis (N), forty-eight hours after suub-cutaneous injection of 10 or 100 μg of ovalbumin.

The results which are shown in Tables 1 and 2 below, testify to the remarkable adjuvant activity of the preparations according to the invention.

TABLE 1

| Adjuvant activities of Mycobacteria preparations | | | | | | | | | |
|---|---|---|---|---|---|---|---|---|---|
| Bacterial Preparation | Dose (μg animal) | Animal | | | | | Presence of granuloma at the point of injection | Cutaneous reaction to ovalbumin average of three animals | |
| | | 1st | 2nd | 3rd | 4th | Average | | 10 μg | 100 μg |
| 0 (FIA) | 0 | 200 | 320 | 140 | 130 | 197 | — | 2 I | 4 I |
| M. butyricum (FCA) | 50 | 3200 | 1600 | 2240 | 4000 | 2760 | + | 10 I 5=18 | (N:E) |
| Substance BB | 10 | 5800 | 4400 | 5600 | 4800 | 5150 | + | | |
| | 2 | 4000 | 2400 | 2480 | 2000 | 2722 | + | 14 I 6=19 | (N:E) |
| Substance $F_I$ | 10 | 5800 | 4400 | 5600 | 4800 | 5150 | + | | |
| Substance $F_{II}$ | 10 | 3600 | 4800 | 7120 | 5500 | 5255 | + | | |
| | 2 | 2880 | 2720 | 3600 | 2800 | 3000 | + | 15 I 7=18 | (N:E) |
| Substance $F_{III}$ | 10 | 3840 | 3600 | 3200 | 2800 | 3360 | + | | |
| Substance G | 10 | 3600 | 5200 | 4400 | 4800 | 4580 | + | | |
| Substance $H_I$ | 25 | 1600 | 1360 | 800 | 1200 | 1240 | + | | |
| Substance $H_{II}$ | 25 | 1040 | 2000 | 2480 | 2080 | 1900 | + | | |
| Substance $H_{III}$ | 50 | 5600 | 4960 | 4240 | 4565 | 4840 | + | | |
| Substance I | 25 | | | | | | + | | |
| Substance J | 25 | 5200 | 4000 | 2800 | 3600 | 3850 | + | | |

TABLE 2

| | Dose/ animal | Antibody/antiovalbumin (μg/ml) N° of animals | | | | | | Hypersensitivity μg ovalbumin | Delayed injection |
|---|---|---|---|---|---|---|---|---|---|
| | | 1 | 2 | 3 | 4 | 5 | Average | 10 | 100 |
| Freund's incomplete adjuvant | 0 | 600 | 660 | 440 | 700 | | 600 | 10 E* | 51* |
| Complete adjuvant | M.butyricum (50 μg) | 4800 | 6160 | 3200 | 4480 | 5040 | 4736 | 10 E | 13 E 7 N* |
| Walls of M.roseus | 25 μg | 3200 | 2400 | 2000 | 2440 | 3200 | 2648 | 8 I | 15 E 4 N |
| Disaccharide pentapeptide of M.roseus | 25 μg | 2480 | 3360 | 3620 | 4640 | 7360 | 4292 | 7 E | 14 E 7 N |
| N-acetylmuramyl-L-Ala-D-Glu-meso-DAP | 25 μg | 4880 | 2560 | 5440 | 1920 | 3840 | 3728 | 7 E | 13 E 5 N |
| N-acetylmuramyl-L-Ala-D-Glu-NH$_2$ | 25 μg | 5280 | 6000 | 2960 | 6880 | 4960 | 5210 | 9 E | 17 E 5 N |

*I = induration, E = erythema, N = necrosis.

The pharmacological tests indicated in Table 2 show:

(a) that the absence of the N-acetyl-glucosamine portion in the osidic part of the fragments of the peptidoglycane concerned does not spoil the adjuvant activity of these fragments;

(b) that the presence of a meso-DAP- group in the peptidic group linked to the osidic portion of the N-acyl-muramic acid, whether the latter is alone or forms part of a longer glycane, is not essential for the preservation of the adjuvant activity of the peptidoglycane fragments concerned.

II. Demonstration of innocuity of the substances according to the invention

The following experiments establish the absence of toxicity of the adjuvant agents according to the invention. They were effected on the substance BB. The conclusions which can be drawn therefrom relative to the innocuity of Substance BB obviously extends to substances $F_I$, $F_{II}$ and $F_{III}$ which are none but constituents thereof.

(1) Hyperreactivity with respect to an endotoxin

Mice were sensitised fourteen days before being challenged with intravenous injections either by 300 µg of BCG (Bacille Calmette-Guérin) killed by phenol, or 300 µg of substance BB. On the day of the test the endotoxin extracted from the Danysz strain of *Salmonella enteritidis* was injected at various doses by the intravenous route. The $LD_{50}$ of this preparation in suspension in isotonic solute and injected in normal controls corresponds to 240 µg.

As shown in Table 3, although all the mice which were treated with 1.5 µg of endotoxin succumbed, in the mice treated with the agent only two deaths in eight were observed, although the endotoxin was injected at 50 µg.

TABLE 3

| Hyperreactivity with respect to an endotoxin | | |
|---|---|---|
| | Endotoxin (µg per mouse) | Deaths/total in |
| | | 24 h. | 48 h. |
| BCG (300 µg i.v.) | 1.5 | 7/8 | 8/8 |
| | 5 | 8/8 | 8/8 |
| | 15 | 8/8 | 8/8 |
| Substance BB (300 µg i.v.) | 50 | 1/8 | 2/8 |

(2) Absence of hyperplasia of the liver and of the spleen

It is well established that when injected by the intravenous route, mycobacteria produced hypertrophy of the liver and of the spleen. All the injections were done by the intravenous route in 0.2 ml and the animals were sacrificed fourteen days later. As seen in Table 4, 300 µg of BCG placed in suspension in an isotonic solution cause considerable splenomegaly. On the other hand, the phenomenon does not occur after an injection of 300 µg of Substance BB.

TABLE 4

| Absence of hypertrophy of the liver or of the spleen after administration of Substance BB | | |
|---|---|---|
| | Number of mice | Weight (mg) |
| | | Soleen | Liver |
| Controls (isotonic solute) | 10 | 143 | 1625 |
| BCG (300 µg i.v.) | 7 | 338 | 1767 |
| Substance BB (300 µg i.v.) | 10 | 148 | 157 |

(3) Absence of arthrogenic action

Injection of Freund's complete adjuvant into the plantar pad of the rat or of the mouse causes very distinct articular oedema. In the following experiment,, groups of ten mice received either Freund's incomplete adjuvant alone (FIA), or Freund's incomplete adjuvant containing 250 µg of *M. tuberculosis* cells or 250 µg of Substance BB. All the injections were done in one of the rear paws in a volume of 0.05 ml. The mice were sacrificed fourteen days later. It was observed that the FIA+Mycobacteria mixture caused a considerable increase in the weight of the injected paw whilst the Substance BB only produced a slight inflammation comparable with that which is observed in the controls which have received FIA only (Table 5).

TABLE 5

| Absence of arthrogenic action in the mouse | | | | |
|---|---|---|---|---|
| | | Weight of the paw in mg | | |
| | Number of mice | Injected | not injected | Difference |
| Controls FIA | 10 | 305 | 222 | 83 |
| FIA + Mycob. (250 µg) | 10 | 892 | 225 | 667 |
| FIA + Substance BB (250 µg) | 10 | 318 | 230 | 88 |

III. Antitumor effect of peritoneal macrophages activated by the substance BB and by the muramyl-dipeptide (N-acetylmuramyl-L-Ala-D-Glu-NH$_2$)

The following test takes advantage of the finding made by several authors that macrophages become cytotoxic with respect to neoplastic cells, when they have previously been activated by immuno-adjuvant substances.

(a) Activation of macrophages in vivo

Two groups of three mice were injected intraperitoneally with 30 µg of each of the substances respectively. The mice were sacrificed 4 days later. There macrophages were recovered according to the technique of D. Juy, C. Bona and L. Chedid, C. R. Acad. Sc. Paris, 1974, 268, Serie D, 1859 and incubated in the presence of tumor cells (mastocytome).

The inhibition of the mastocytome increase was measured by reference to the reduced incorporation of radioactive thymidine as compared to that of controls. The substance BB and the muramyl-dipeptide induced a 75% and 84% inhibition respectively, this corresponding to a marked cytotoxic effect of the corresponding macrophages.

(b) Activation in vitro

The activity of the muramyl-dipeptide was measured by directly incubating it with both normal macrophages and macrophages originating from an inflammatory peritoneal exsudate. The muramyl-dipeptide was shown to be capable of increasing in vitro the cytotoxicity of the macrophages with respect to the mastocytome in both cases.

IV. Absence of delayed hypersensitivity with respect to the BB substance and the muramyl-dipeptide in guinea pigs treated with the complete Freund's adjuvant Three groups of guinea pigs were injected (in their foot pads) with 1 mg of ovalbumine together with:
(a) Freund's incomplete adjuvant (FIA) and
(b) Freund's complete adjuvant (FCA) respectively.

The delayed hypersensitivity was measured by subcutaneous reaction three weeks thereafter, by injecting 5 mg of ovalbumine and of 5 and 10 µg of either the substance BB and the muramyl-dipeptide in the dermis of the animals. The animals of group (b) exhibited a strong reaction to the ovalbumine. In contradistinction thereto, the two tested substances dit not induce any detectable reaction. Therefore they do not exhibit tuberculine like sensitizing properties.

It should finally be noted that the muramyl-dipeptide exhibited no detectable toxicity when administered under a 30 µg dosage to surrenalectomized mice.

Thus adjuvant substances which can be used for increasing the efficiency of vaccines of bacterial or viral origin are obtained, more particularly if the vaccines are weak immunogens. They may be used in particular for enhancing immunisation of the host (human or animal patients) with regard to infections of bacterial or viral origin, antigens of tumours, protozoan antigens, etc. They may also be used effectively for the production of serums containing antibodies. They may be administered with the above-mentioned antigen or vaccines or antibodies in pharmaceutically acceptable sterile water in oil emulsions.

For example the substances according to the invention may be suspended in incomplete Freund's adjuvant or in a vehicle constituted by 8.5 parts of hexadecane, 1.5 parts of sorbitan dilaurate, known under the trademark ARLACEL, or glycerol monooleate, and 10 parts of isotonic solution.

It is finally of special interest to note that the substances according to the invention can, under suitable conditions of use, exhibit their adjuvant activity even when they have been added to the antigen in saline solution.

It will be observed lastly, that administration of the substances can be carried out in the form of typical compositions of the vaccine type, by intramuscular, intradermal or subcutaneous injection, as well as by scarification.

We claim:

1. A peptidoglycan, N-Acmuramyl of the formula

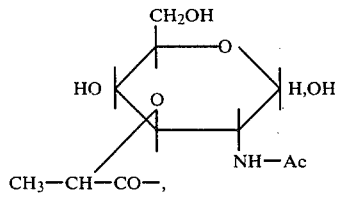

to which carboxyl group there is linked a peptide chain which comprises two to eight aminoacid residues, the first aminoacid residues comprising alanyl, seryl, or glycyl, and the second aminoacid residues comprising glutamic or aspartic acid residues, the carboxyls of this second aminoacid residue being either free or substituted, or when there are more than two aminoacid residues, the carboxyls of the second aminoacid being either free, substituted or linked to another aminoacid residue, with the proviso that both carboxyls of the second aminoacid are not free and Ac methyl, concurrently.

2. N-acetylmuramyl-L-alanyl-D-alpha-isoglutamine.

3. The Acmuramyl of chain 1 wherein the peptide chain comprises 2 to 5 aminoacids.

4. The Acmuramyl of claim 3 wherein the peptide chain comprises 2 aminoacids.

5. The Acmuramyl of claim 3 wherein the second aminoacid residue of the peptide chain is glutamic.

6. The Acmuramul of claim 5 wherein the glutamic residue is D-glutamic.

7. The Acmuramyl of claim 3 wherein the first aminoacid residue of the peptide chain is alanine.

8. The Acmuramyl of claim 3 wherein the first and second aminoacid residue is alanine and glutamic, respectively.

9. The Acmuramyl of claim 3 wherein the aminoacid residue is in its L- or in its D- forms.

10. The Acmuramyl of claim 7 wherein the second aminoacid residue is L-aspartic.

11. The Acmuramyl of claim 5 wherein the second aminoacid being glutamic, the carboxyls are either free or substituted.

12. The Acmuramyl of claim 11 wherein the first of the two aminoacid residues is L-alanine.

13. The Acmuramyl of claim 11 wherein it is the alpha-carboxyl of the glutamic which is free or substituted.

14. The Acmuramyl of claim 13 wherein the substitution in the alpha-carboxyl is amido.

15. The Acmuramyl of claim 11 wherein the glutamic is D-glutamic.

16. The Acmuramyl of claim 8 wherein the peptide which has more than two aminoacid residues is selected from the group consisting of the following aminoacid residues: meso-DAP, D-alanine, D-glutamic and L-alanine, the first two residues being of D-glutamic and L-alanine.

17. The Acmuramyl of claim 3 wherein the peptide which has more than three aminoacid residues is selected from the group consisting of the following aminoacid residues: L-threonine, L-lysine and D-alanine.

18. The Acmuramyl of claim 3 wherein the first aminoacid residue is serine.

19. The Acmuramyl of claim 3 wherein the peptide chain comprises more than two aminoacid residues, the additional aminoacid residue being linked to the gamma-carboxyl of the second aminoacid residue.

20. A compound of the formula

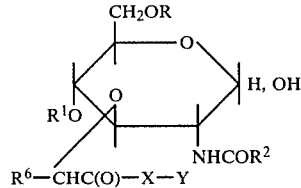

wherein $R^6$ is methyl, R and $R^1$ are each hydrogen, $R^2$ is methyl or hydroxymethyl, X is selected from the group consisting of L-alanyl, L-seryl or glycyl, and Y is D-isoglutamine.

21. The compound of claim 20 wherein X is L-alanyl or L-seryl.

22. The compound of claim 20 wherein $R^2$ is methyl.

23. The compound of claim 20 wherein $R^2$ is hydroxymethyl.

24. The compound of claim 20 wherein R and $R^1$ are both hydrogen, $R^2$ is methyl, X is L-alanyl and Y is D-isoglutamine.

25. The compound of claim 20 wherein R and $R^1$ are both hydrogen, $R^2$ is methyl, X is L-seryl and Y is D-isoglutamine.

26. The compound of claim 20 wherein R and $R^1$ are both hydrogen, $R^2$ is hydroxymethyl, X is L-alanyl and Y is D-isoglutamine.

27. The compound of claim 20 wherein R and $R^1$ are both hydrogen, $R^2$ is hydroxymethyl, X is L-seryl and Y is D-isoglutamine.

28. The peptidoglycan of claim 1 wherein -Ac is acetyl, the first aminoacid residue being L-alanine and the second residue being D-glutamic.

* * * * *